US006469784B2

United States Patent
Golberg et al.

(10) Patent No.: US 6,469,784 B2
(45) Date of Patent: Oct. 22, 2002

(54) OPTICAL INSPECTION METHOD AND APPARATUS UTILIZING A VARIABLE ANGLE DESIGN

(75) Inventors: Boris Golberg, Asdhod; Amir Komem, Tel Aviv; Ron Naftali, Kiriat-Ono; Gilad Almogy, Givatayim, all of (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/941,659

(22) Filed: Aug. 30, 2001

(65) Prior Publication Data

US 2002/0005947 A1 Jan. 17, 2002

Related U.S. Application Data

(63) Continuation of application No. 09/330,249, filed on Jun. 10, 1999, now Pat. No. 6,366,352.

(51) Int. Cl.⁷ .............................................. G01N 21/00
(52) U.S. Cl. .............................. 356/237.2; 356/237.3
(58) Field of Search ............................ 356/237.1–237.5, 356/239.1, 239.2, 239.3, 239.8, 364, 369; 250/572, 562, 563, 559.48, 559.01, 559.09; 382/30, 31

(56) References Cited

U.S. PATENT DOCUMENTS

| 3,813,172 A | 5/1974 | Walker et al. .............. 356/225 |
| 3,972,616 A | 8/1976 | Minami et al. ............... 356/71 |
| 4,669,875 A | 6/1987 | Shiba et al. ................. 356/237 |
| 4,898,471 A | 2/1990 | Stonestrom et al. ........ 356/394 |
| 4,902,131 A | 2/1990 | Yamazaki et al. .......... 356/336 |
| 5,046,847 A | 9/1991 | Nakata et al. .............. 356/338 |
| RE33,956 E | 6/1992 | Lin et al. .................... 250/550 |
| 5,172,000 A | 12/1992 | Scheff et al. ............... 250/550 |
| 5,177,559 A | 1/1993 | Batchelder et al. ......... 356/237 |
| 5,276,498 A | 1/1994 | Galbraith et al. ........... 356/237 |
| 5,471,066 A * | 11/1995 | Hagiwara ............... 250/559.48 |
| 5,604,585 A | 2/1997 | Johnson et al. ............ 356/237 |
| 5,623,340 A * | 4/1997 | Yamamoto et al. ........ 356/237 |
| 5,712,701 A | 1/1998 | Clementi et al. ........... 356/237 |
| 5,963,314 A | 10/1999 | Worster et al. .......... 356/237.2 |
| 6,034,776 A | 3/2000 | Germer et al. ............. 356/369 |
| 6,064,477 A * | 5/2000 | Matsumoto et al. ........ 356/237 |

FOREIGN PATENT DOCUMENTS

EP        0 780 670 A1    6/1997

OTHER PUBLICATIONS

Omer Carmel et al. "New directions in process control" Proceedings of the SPIE, vol. 2196/333, 1994, XP–002119843.

* cited by examiner

Primary Examiner—Michael P. Stafira
(74) Attorney, Agent, or Firm—Sughrue, Mion, Zinn, MacPeak & Seas

(57) ABSTRACT

Method and apparatus for optical inspection of an article are presented. The apparatus comprises an illumination unit and at least one detection unit. The illumination unit generates an incident beam and directs it onto a predetermined region of the article. The detection unit includes a light collection system and a detector. The light collection system collects light scattered from the illuminated region with a predetermined constant maximum collection angle, and utilizes a variable angle design for selectively selecting from collected light at least one light component propagating with a solid angle segment of the maximum collection angle, and directing it to the detector.

24 Claims, 8 Drawing Sheets

OPTICAL INSPECTION METHOD AND APPARATUS UTILIZING A VARIABLE ANGLE DESIGN

This is a continuation of application Ser. No. 09/330,249 filed Jun. 10, 1999 now U.S. Pat. No. 6,366,352, the disclosure of which is incorporated herein by reference.

FIELD OF THE INVENTION

The present invention is in the field of automatic optical inspection techniques and relates to a method and an apparatus for inspecting articles utilizing a variable angle design.

BACKGROUND OF THE INVENTION

The manufacture of various articles, such as integrated circuits, printed circuit boards, photolithographic masks, etc., requires them to be automatically inspected during progress on a production line. The timely detection of anomalies on the surface of such article is a very important factor subsequently leading to an increase in production yields.

Semiconductor wafers are inspected prior to and after patterning procedure. Optical inspection systems typically employ such main constructional parts as illumination optics and collection-detection optics for, respectively, directing incident light from a light source onto the wafer to be inspected, and collecting light returned (scattered, reflected) from the wafer and directing the collected light onto a sensing means.

Prior-to-patterning inspection of wafers relies on the fact that light is scattered mainly from anomalies present on the generally flat and smooth surface of the non-patterned wafer. Thus, any detection of scattered light may be indicative of a defect.

However, when inspecting patterned wafers, scattered light can be caused by the pattern. Therefore, the detection of scattered light is not necessarily indicative of a defect. In order to detect defects on a patterned surface, templates formed by signals representative of detected light components scattered from periodic features of the pattern (i.e. dies of the wafer) are typically constructed and compared. Differences between the signals are indicative of light scattered from anomalies present on the surface of the article, and are therefore detected as defects. Another technique, so-called "die-to-die" inspection, consists of comparing light scattered from an individual die to that of its "neighbor". Any detected difference in light components scattered from these two dies, is indicative of the absence or addition of some features in one of the dies as compared to the other, and is therefore considered to be a defect.

To facilitate meaningful signal comparison, i.e. to successfully analyze the signals associated with different dies and cells of the wafer, it is desirable for the light collection system to collect light at one constant collection angle. The advantages of a single constant collection angle based technique are disclosed, for example, in U.S. Pat. Nos. 4,898,471 and 5,604,585, both of which relate to systems for detecting particles on the surface of a patterned article.

SUMMARY OF THE INVENTION

There is a need in the art to improve the conventional inspection techniques by providing a novel method and apparatus for optical inspection of articles utilizing a variable angle design.

It is a major feature of the present invention to provide such an apparatus that enables the signal-to-noise ratio of the detected signal to be significantly increased.

The main idea of the present invention is based on the following. An article (e.g., wafer) under inspection is scanned region-by-region, and light scattered from each of the scan regions is collected with a certain maximum collection angle constant for each scan region. The maximum collection angle is a solid angle having a certain value and a certain central direction defined by a light collecting optics. A filter is selectively operable in the optical path of the collected light for selectively separating therefrom at least one light component propagating with a predetermined solid angle segment of the maximum collection angle.

If any unexpected difference (defect) is detected at a specific location or, on the contrary, a probability of a defect exists at a specific location on the article (according to previous knowledge of the pattern structure of the article, which is typically the case), this location is inspected by varying (reducing) the collection angle. At this specific location, namely for this specific scan region, one or more light components of the collected light could be captured and directed on a detector, thereby increasing the signal-to-noise ratio of the detected signal. If the article has a repetitive pattern, this pattern scatters light into a specific angular range according to the specific pattern characteristics. The signal-to-noise ratio of the detected signal can be improved by preventing light propagating within this specific angular range from being detected.

There is thus provided according to one aspect of the present invention an apparatus for optical inspection of an article, comprising an illumination unit generating an incident radiation and illuminating a predetermined region on the article, and at least one detection unit, wherein said at least one detection unit comprises:

(a) a light collecting optics that collects light scattered from the illuminated region with a predetermined constant maximum collection angle;

(b) a filter selectively operable in the optical path of the collected light for selectively separating therefrom at least one light component propagating with a predetermined solid angle segment of the maximum collection angle; and (c) detector having a sensing surface for receiving collected light and generating data representative thereof.

The illumination unit may be oriented so as to illuminate the article either normally or at a grazing angle. The at least one detection unit operates in a perspective dark field imaging mode.

The filter may comprise a mask assembly. The mask assembly may be composed of a plurality of different masks mounted so as to enable a selected one of the masks to be installed in the optical path of the collected light propagating towards the detector. The filter may be a programmable LCD or a micro electro-mechanical structure (MEMS).

The light collecting optics is designed so as to form an angular image of the illuminated region. The term "angular image" signifies such an image of an object, wherein each point of the image corresponds to an angle formed by light coming from any point of the object. In other words, the collected light ensuing from the light collecting optics is representative of the angular image of the illuminated region formed by the light scattered from the illuminated region and propagated with the certain constant solid angle. The collected light representative of the angular image of the illuminated region is transmitted to the detector.

The light collecting optics comprises first and second optics. The first optics defines the maximum collection angle and is capable of forming a real image of the illuminated region, while the second optics is capable of forming from this real image an angular image of the illuminated region. To ensure that the real image is formed from light components coming from the illuminated region only, the light collecting optics also comprises a slit with a shape and dimensions substantially identical to those of the real image which is mounted substantially at the expected location of this image. This enables any light component coming from a location outside the illuminated region to be prevented from reaching the detector. Hence, the signal-to-noise ratio of detected light is increased even more, considering "noise" as any light component other than that scattered from the illuminated region with the maximum collection angle.

Preferably, the detection unit also comprises an additional optical system accommodated in the optical path of the collected light propagating towards the detector, and is capable of directing said light onto the entire sensing surface of the detector. This enables an undesirable dependence between the detected differences in output signals produced by the detector and typical non-uniformity of its sensitivity distribution to be avoided. Preferably, this additional optical system utilizes a telecentric-imaging mode.

Thus, according to another aspect of the present invention, there is provided an apparatus for optical inspection of an article, comprising an illumination unit generating an incident radiation and Illuminating a predetermined region on the article, and at least one detection unit, wherein said at least one detection comprises:

a light collecting optics that collects light scattered from the illuminated region with a predetermined constant maximum collection angle;
a filter selectively operable in the optical path of collected light for selectively separating therefrom at least one light component propagating with a predetermined solid angle segment of the maximum collection angle; and
an optical system imaging collected light onto the entire sensing surface of a detector.

The detection unit may also comprise a polarizer accommodated so as to be displaceable between its two extreme positions, being, respectively, in and out of the optical path of the collected light propagating towards the detector. The polarizer, when positioned in the optical path, may also be displaceable so as to change the orientation of the plane of its preferred transmission.

Preferably, the detection unit also comprises an image transmission means capable of transmitting the collected light to a desired location of the detector in a manner to avoid any distance-introduced changes of the image. The image transmission means may comprise an imaging fiber bundle formed of a plurality of coherent fibers, or alternatively, may comprise relay optics.

The present invention, due to the above light collecting technique, allows for significantly increasing signal-to-noise ratio in the detected light, "noise" being considered as any light component other than those scattered from the illuminated region with the maximum collection angle. By using more than one detection unit constructed as described above and having light directing optics positioned so as to collect light propagating with different azimuth angles, the defects on the surface of the article are not only detected, but are also successfully classified. The term "azimuth angle" signifies an angle between the direction of an incident beam and that of a returned beam, as seen from the top view. Additionally, due to the provision of the filter, the present invention allows for varying the azimuth and/or elevation angles from their maximum values defined by the light collecting optics. The term "elevation angle" signifies an angle between the direction of a scattered light component and the scattering surface, as seen from the side view. This angles' variation enables differences in the light components representative of the certain angular image of the illuminated region, but propagating with different solid angle segments of the maximum collection angle, to be detected. The provision of the polarizer enables the signal-to-noise ratio to be increased even more, considering the "polarized noise".

More specifically, the present invention is used for inspecting wafers and is therefore described below with respect to this application.

BRIEF DESCRIPTION OF THE DRAWINGS

In order to understand the invention and to show how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
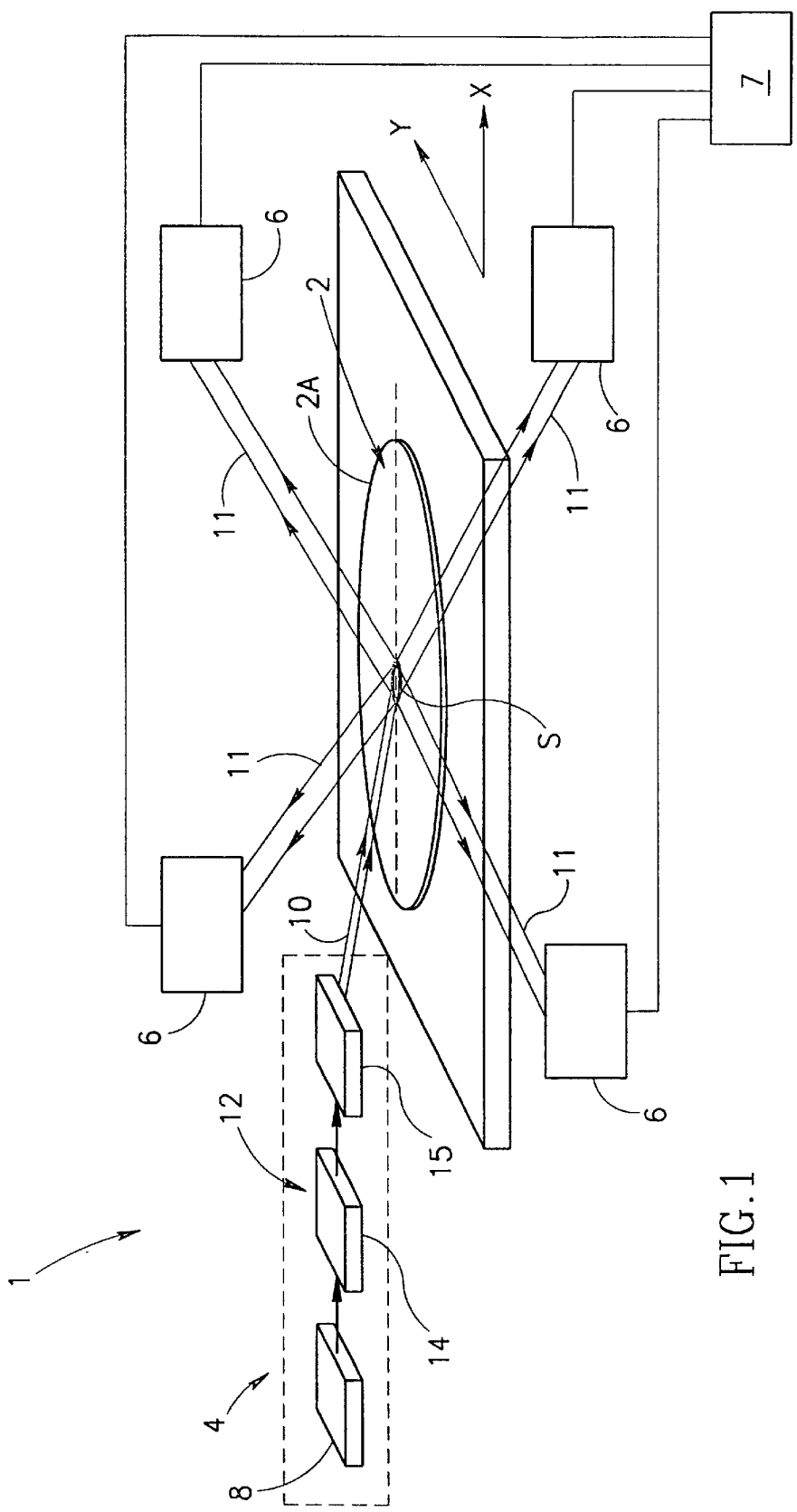
FIG. 1 is a schematic block diagram illustrating the main components of an apparatus constructed according to one embodiment of the invention.

Referring to FIG. 1, there is illustrated an optical inspection apparatus, generally designated 1, associated with a wafer 2 to be inspected. The upper surface 2a of the wafer 2 may or may not be formed with a pattern, which is therefore not specifically shown. The apparatus 1 comprises an illumination unit, generally at 4, and four detection units, generally at 6, operating in a perspective dark field imaging mode. Output circuits (not shown) of the detection units 6 are coupled to a processor 7. which is appropriately equipped with hardware and is operated by suitable software, so as to successfully analyze data coming from the detection units 6. The construction and operation of the processor 7 do not form a part of the present invention and may be of any known kind.

The illumination unit 4 comprises a light source 8, for example a laser, emitting a beam of light, generally at 10, and a light directing optics 12. The light directing optics 12 comprises a suitable scanning means 14 (for example an acousto-optic element) mounted in the optical path of the beam 10, and a focusing optics 15. The acousto-optic element 14 causes the beam 10 to scan along the wafer. Obviously any other suitable scanning means may be used, for example a rotating mirror. It should be noted that the provision of any scanning means is optional, and a non-scanning beam could be used for the same purpose, i.e. for illuminating a line on the surface of the wafer. The focusing optics 15 is typically a lens or a plurality of lenses (not shown). The scanning means 14 and focusing optics 15 operate together to focus the beam 10 onto a scan line S (constituting an illuminated region) on the surface 2a. The propagation of light is shown here schematically solely in order to facilitate the illustration of the main components of the apparatus 1.

The construction and operation of the illumination unit 4 are known per se and therefore need not be described in more detail, except to note the following. According to the present example of FIG. 1, the illumination unit 4 provides the scanning of the article 2 at a substantially grazing angle relative to its surface 2a. It is understood, although not specifically shown, that the light source 8 may be accommodated at any other appropriate location relative to the surface 2a, provided the light directing optics 12 includes a mirror or the like to form the desired angle of incidence of the scanning beam 10.

Figure 2:
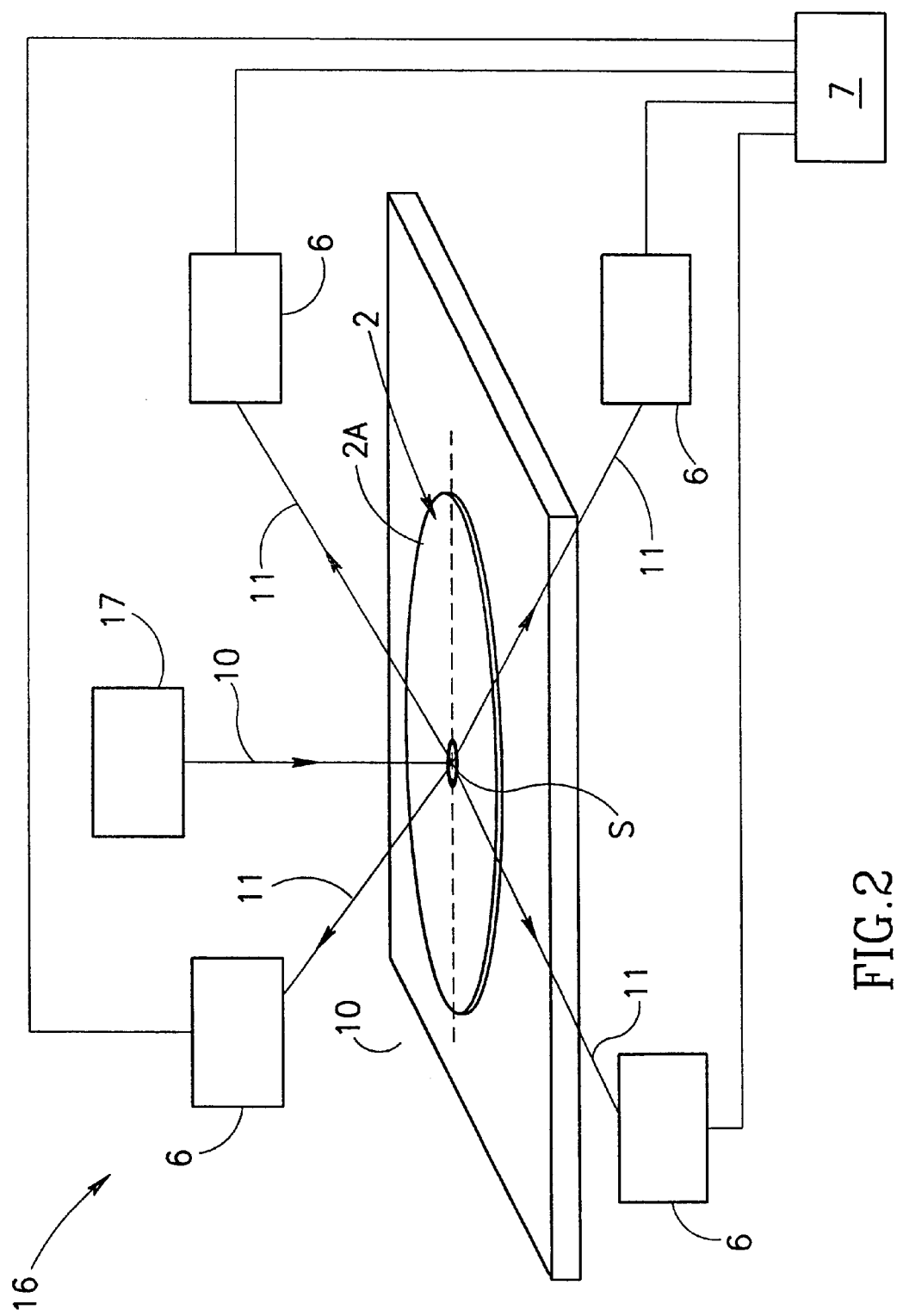
FIG. 2 is a schematic block diagram illustrating the main components of an apparatus constructed according to another embodiment of the invention.

FIG. 2 illustrates an apparatus, generally designated 16, having a somewhat different construction in comparison to that of the apparatus 1. The same reference numbers are used to indicate those components that are identical in the devices 1 and 16, in order to facilitate understanding. As shown, an illumination unit 17 of the apparatus 16, as distinct from that of the apparatus 1, provides a substantially normal direction of the incident light 10 relative to the surface 2a.

In both examples the laser beam 10 is caused to move in a scanning direction (i.e. along the X-axis), while the wafer 2 is supported on a translational stage (not shown) for movement along the Y-axis. Each of the detection units 6 operates in a perspective dark field imaging mode, i.e. collects light components, generally at 11, scattered from the surface 2a at azimuth and elevation different from those where the most specular reflection occurs, wherein the specular reflected light propagates within a certain solid angle.

Figure 3:
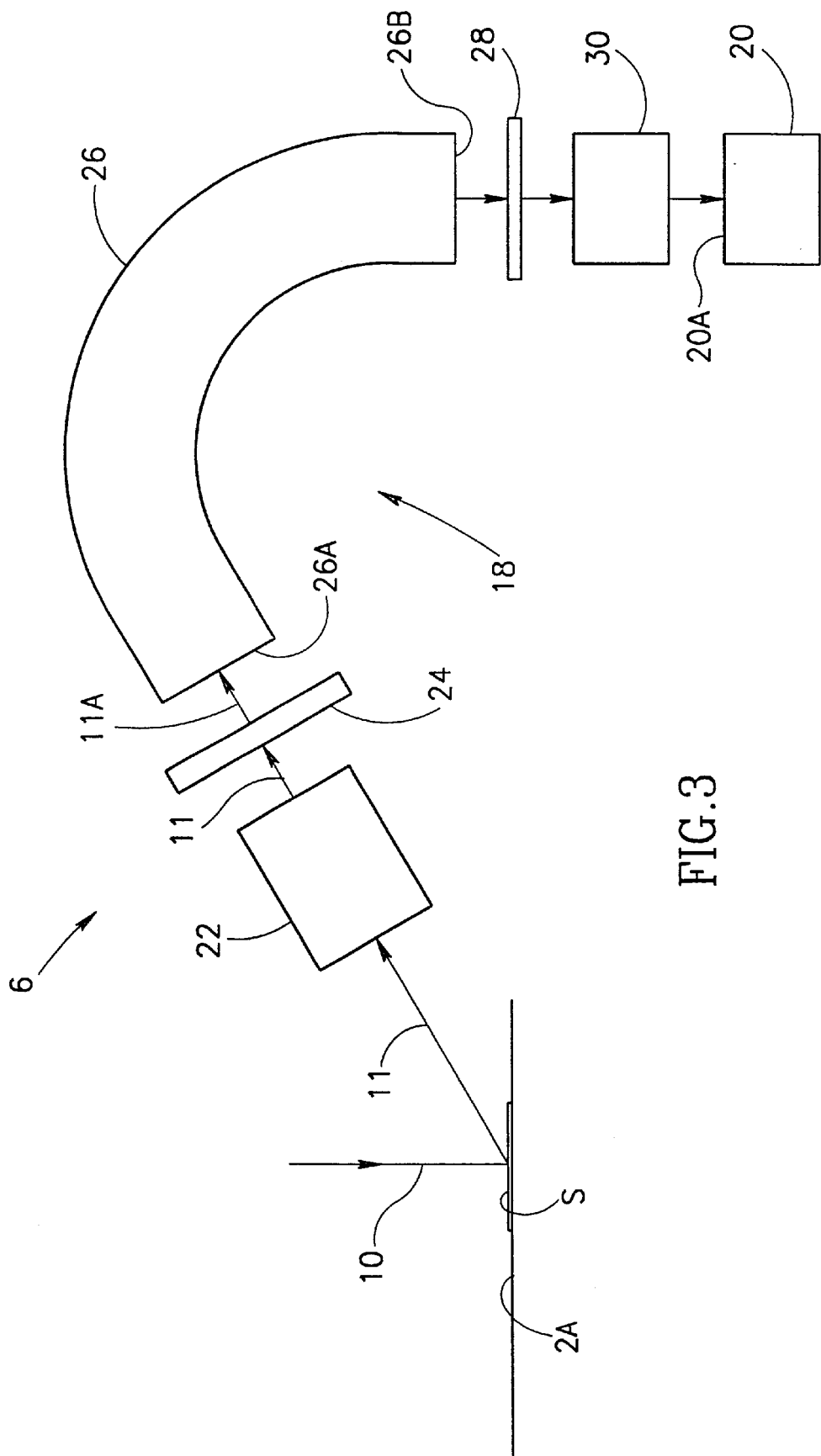
FIG. 3 is a schematic block diagram more specifically illustrating the main components of a detection unit, constructed according to one example of the present invention, suitable for the apparatus of either of FIGS. 1 or 2.

The four detection units 6 have similar constructions and therefore the main components of only one of them are illustrated in FIG. 3. The detection unit 6 comprises a light collection system 18 and a detector 20 which may be of any suitable kind, for example a photomultiplier tube (PMT) whose construction and operation are known per se.

In the exemplified preferred embodiment, the light collection system 18 includes collecting optics 22, a coherent (imaging) fiber bundle 26 (constituting image transmission means) and a mask assembly 28 (constituting a filter) which is followed by an optical system 30. While not a necessary element, the preferred embodiment includes a polarizer 24 inserted in the light path of the optics 22.

The principles of operation of the coherent fiber are known per se and therefore need not be specifically described, except to note the following. A coherent fiber bundle is used for transmission of images. The relative positions of individual fibers in the coherent fiber bundle is maintained, and, due to this fact, the fiber bundle provides desired linear correlation between input and output signals. The construction and operation of the mask assembly 28 and optics 30 will be described more specifically further below with references to FIGS. 5 and 6, respectively.

The incident light 10 impinges onto the scan line S and is scattered by the pattern and anomalies that may occasionally occur on the surface 2a within the scan line S. The light components 11 that are scattered from the scan line S and propagate with a certain solid angle are collected by the optics 22 and directed into the polarizer 24. The polarizer 24 is operated by a suitable driver (not shown) for movement in a manner to be positioned either in or out of the optical path of the light ensuing from the collecting optics 22. Additionally the polarizer 24, when being installed in the optical path, is rotatable in a manner to change the orientation of the plane of its preferred transmission (preferred polarization). The displacement of the polarizer 24 affects the light 11a passing therethrough. Since the pattern may have high polarization degree representing a so-called "polarized noise", the displacement of the polarizer affects the signal-to-noise ratio in the light component 11a propagating towards the detector. Additionally, a learning mode may be applied to the specific kind of article prior to its inspection. This enables a certain polarization signature in the light component returned from the pattern to be expected and, therefore, by changing the orientation of the polarizer 24, to detect differences (defects), if any.

Figure 4:
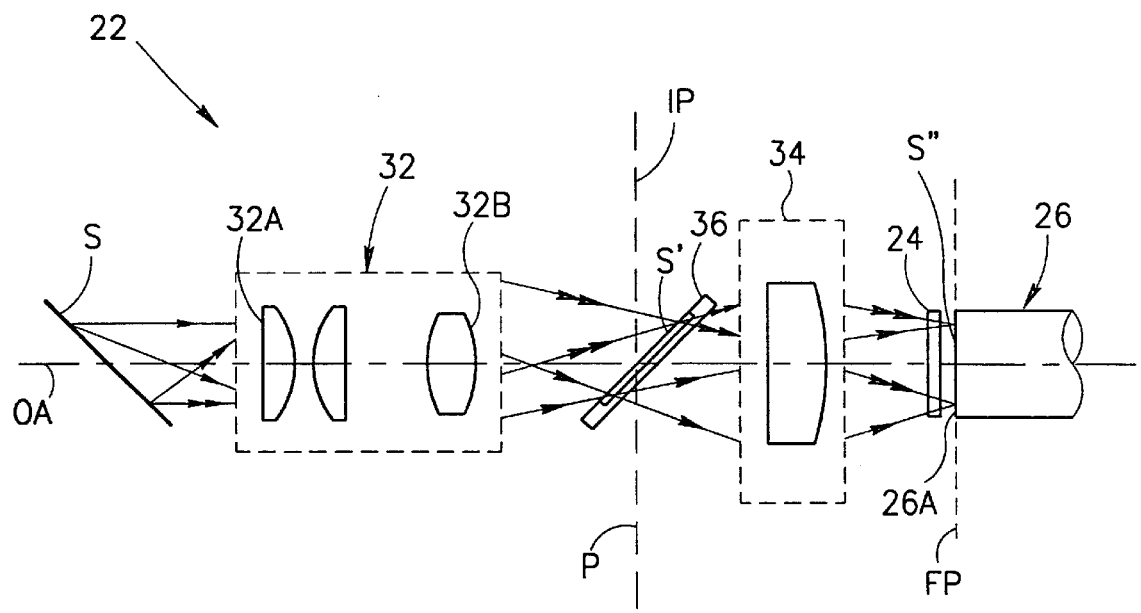
FIG. 4 is a beam diagram illustrating the main principles of operation of light collecting optics of the detection unit of FIG. 3.

Turning now to FIG. 4, the light collecting optics 22 comprises a first lens assembly 32 (constituting a first optics) and a second lens assembly 34 (constituting a second optics), and a slit 36 located in a front focal plane P of the lens assembly 34. The light propagation through the lens assemblies 32 and 34 defines an optical axis OA. The lens assembly 32 is positioned to collect light components scattered from the scan line S and propagating with a certain solid angle. The dimensions of a first glass surface 32a of the lens assembly 32 defines the value of the solid angle of collection of the optics 22, which is the maximum collection angle of the entire detection unit 6.

The light collecting optics 22 is designed so as to form an angular image of the scan line S which is transmitted towards the detector 20 through the fiber bundle 26. The lens assembly 32 is designed to form a real image S' of the scan line S in an image plane IP. The image plane IP substantially coincides with the front focal plane P of the lens arrangement 34. The slit 36 is shaped and dimensioned similar to that of the real image S', and is installed at the location of the expected image. As for the lens assembly 34, it forms from the real image S' of the scan line S an angular image S" thereof. Each point of the angular image S" is formed by a light component coming from any point of the scan line S and propagating with a segment of the maximum collection angle. Each such segment of the maximum collection angle is transmitted towards the detector through one or more corresponding fibers of the fiber bundle 26.

The provision of the slit 36 is based on the following. The illumination unit, due to unavoidable reflection occurring therein, typically produces an additional undesirable image of the scan line (a so-called "ghost") on the surface of the wafer. This undesirable image would also generate returned light propagating towards the light collecting optics. The slit 36 so designed and positioned allows the passage of the collected light representative of the real image S' of the scan line S to the lens assembly 34, and blocks the passage of any light other than that associated with the image S'.

A surface 26a defined by the front end (with respect to light propagation) of the fiber bundle 26, is located in a focal plane FP of the entire collecting optics 22, defining thereby the most desirable location for the system's entrance pupil. Such a design of the collecting optics 22 and its position relative to the fiber bundle 26 enable the resolution of the light collection system 18 to be significantly increased, and allows for optimizing the fiber bundle operation. The diameter of the fiber bundle 26 preferably slightly exceeds that defined by the cone of the maximum collection angle, so as to allow all the collected light beams (i.e. all the solid angle segments of the maximum collection angle) to enter the fiber bundle 26.

Thus, the light collecting optics 22 forms the angular image S" of the scan line S, and directs the collected light representative of this image into the fiber bundle 26. Each point of the image S" is representative of a certain angle of propagation of the collected light component (within the maximum collection angle) scattered from any point on the scan line S. Each angular light component is projected onto a corresponding point (fiber) on the input surface 26a of the fiber bundle 26, and is transmitted by the fiber bundle into the same angle ensuing from the corresponding point on an output surface of the fiber bundle.

The above design of the light collecting optics 22 enables to significantly improve the signal-to-noise ratio of the collected light entering the fiber bundle 26, "noise" being considered as any light component other than those scattered from the scan line within the maximum collection angle and forming the desired angular image S" of the scan line S. Moreover, this technique ensures the same field of view of all points along the scan line S, and of all the detection units 6, thereby increasing the signal-to-noise ratio in difference-indicative signals that can be detected when comparing data generated by all the detection units 6.

Figure 5:
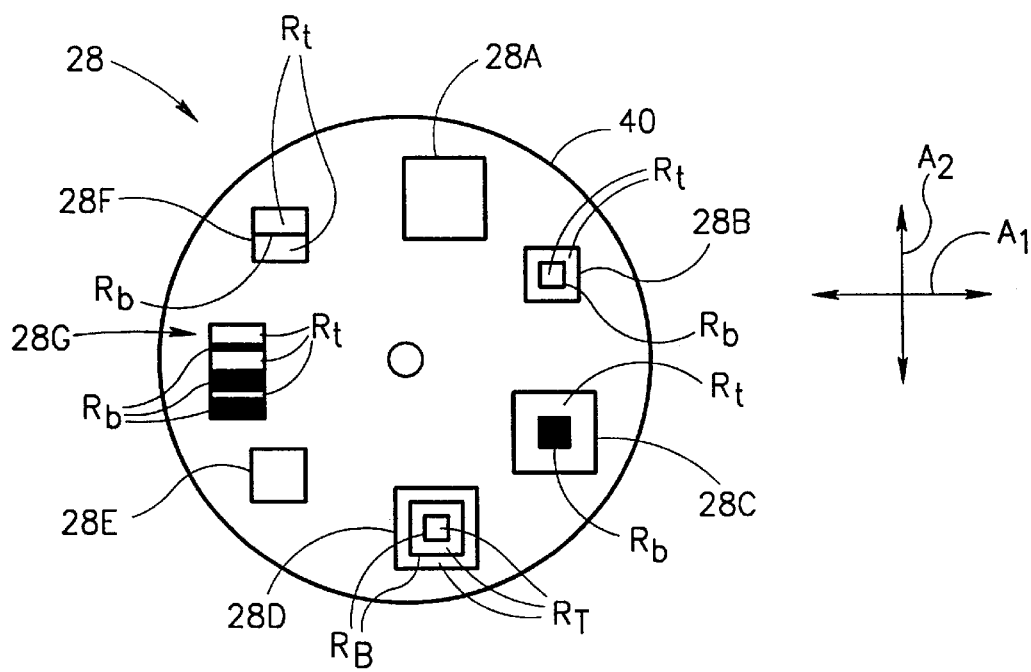
FIG. 5 more specifically illustrates a mask assembly suitable for the detection unit of FIG. 3.

Turning now to FIG. 5, the mask assembly 28 is composed of several differently designed masks, seven in the present example, designated respectively 28a–28g, which are formed in a common disc-like opaque plate 40. This may be, for example, a metal disk with holes or a glass-with-chrome mask. The disc 40 is operated by its motor, which is not specifically shown here, for rotation in a plane perpendicular to the long axis of the fiber bundle so as to selectively locate the desired one of the masks in the optical path of the propagating light 11a (FIG. 3). Hence, in the operational position of the mask assembly 28, one of the masks 28a–28g is installed in the optical path of the light ensuing from the fiber bundle 26.

Each of the masks 28a and 28e represents an aperture that defines a certain solid angle of collection smaller than the maximum collection angle defined by the first glass surface 32a of the lens arrangement 32. By placing one of the masks 28a and 28e in the optical path of the light ensuing from the fiber bundle 26, one certain solid angle segment of the maximum collection angle may be picked out. Generally speaking, each of the masks defines at least one transmitting region $R_t$ with respect to the collected light. Alternatively, although not specifically shown, a single mask having variable dimensions could be used.

The masks 28b, 28c, 28d, 28f and 28g have different patterns, each formed of regions $R_t$ and $R_b$, which are, respectively, transmitting and blocking with respect to the light impinging on the mask. Each of these masks, when in its operative position (i.e. located in the optical path of the light ensuing from the fiber bundle), is capable of cutting off and picking out one or more solid angle segments.

More specifically, the mask 28c cuts off a central portion (defined by the blocking region $R_b$ of this mask) of the solid angle formed by light impinging on the mask, while allowing the propagation of a periphery cone segment (defined by the transmitting region $R_t$ of the mask). The mask 28b would pick out two solid angle segments defined by the dimensions of two transmitting regions $R_t$, wherein these solid angle segments are spatially separated in accordance with the dimensions of the blocking regions $R_b$. The mask 28d would pick out three spatially separated solid angle segments, allowing their propagation towards the detector. The masks 28f and 28g would, respectively, pick out two and three spatially separated solid angle segments, but by means of cutting off one and two elongated portions of the incident solid angle.

The provision of the mask assembly comprising several different masks allows for selectively varying the collection angle of the entire detection unit 6, thereby enabling the differences, if any, to be detected. To this end, knowledge of the wafer's pattern prior to its inspection is desired, so as to apply the angle variation to those locations on the wafer where the existence of defects is possible, or where an "unexpected" defect-indicative signal is suddenly detected. It is important to note that such a mask assembly provides for solid angle variations simultaneously along two mutually perpendicular axes, shown as $A_1$ and $A_2$ in FIG. 5. By selecting an appropriate mask, the specularly reflected light components, for example associated with 45° or 90° geometries of the pattern, could be prevented from being sensed by the detector 20.

Figure 6:
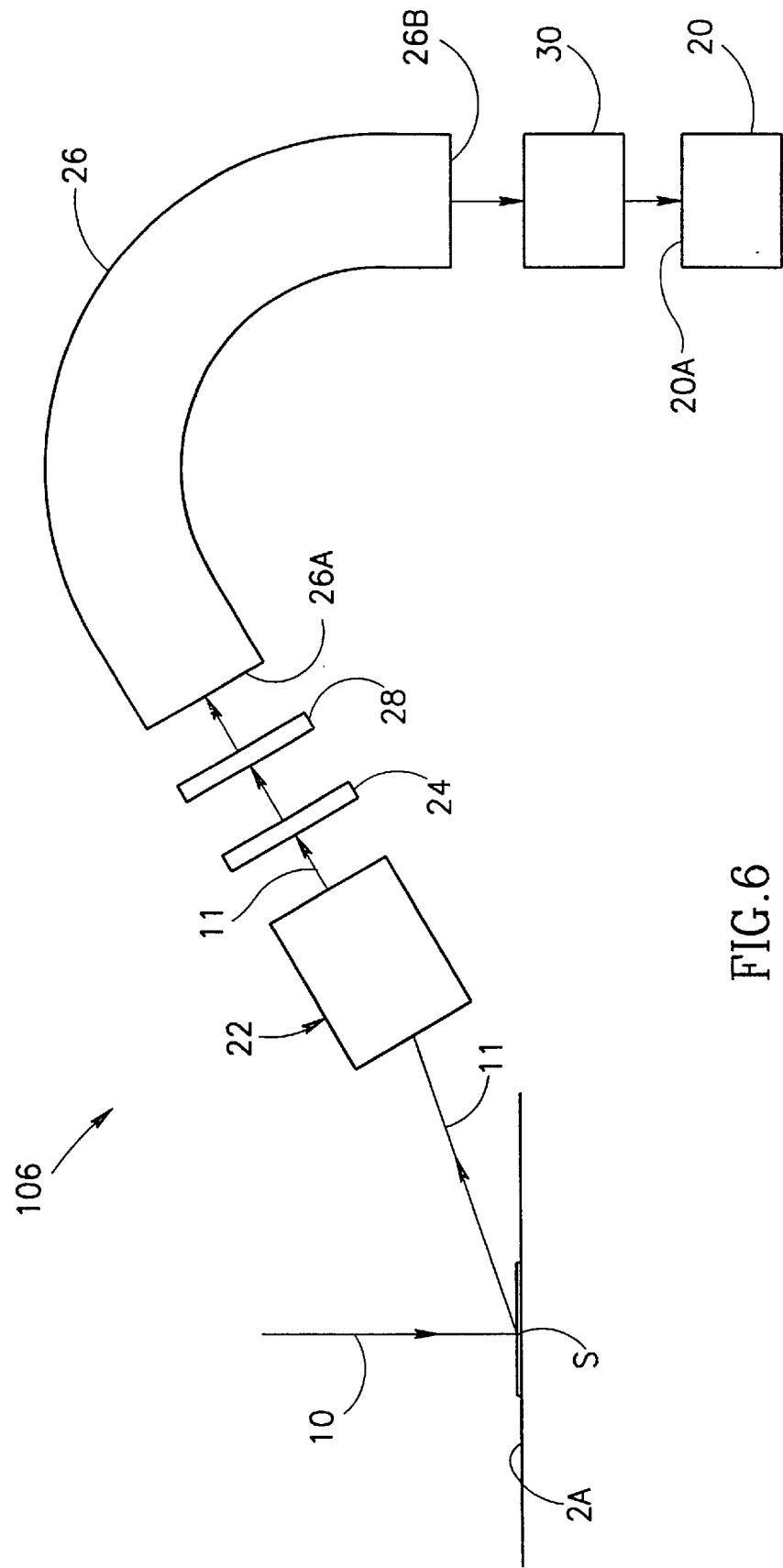
FIGS. 6 and 7 are schematic block diagrams illustrating the main components of detection units constructed according to two more examples of the present invention, respectively, suitable for the apparatus of either of FIGS. 1 or 2.

According to the above example of FIG. 3, the mask assembly 28 is mounted in the proximity of the output surface 26b of the fiber bundle 26. FIG. 6 illustrates another example of a detection unit, generally designated 106, suitable for use with the inspection apparatus 1 or 16. Similarly, those components which are identical in the units 6 and 106, are identified by the same reference numbers. In the detection unit 106, the fiber bundle 26 is located directly after the mask assembly 28. In this case, the mask assembly 28 is located in the focal plane FP of the light collecting optics 22. When the mask assembly is mounted upstream of the fiber bundle, the light component propagating within the selected collection angle is transmitted by the corresponding fiber towards the detector. It should be noted that in the example of FIG. 6, the fiber bundle 26 may and may not be an imaging fiber.

Generally, the dimensions of a selected mask depend on the numerical aperture of an objective lens used in the optical inspection apparatus. Hence, the filter should preferably comprise a set of masks (which may or may not be made in a common disk) to meet the requirements of all possible objective lenses.

It should be noted, although not specifically shown, that a mask assembly comprising a plurality of various masks may be designed like a continuous pattern formed by transparent and opaque regions and extending along a circumferential region of a disc-like plate. Each portion of the pattern is formed by a different combination of locally adjacent transmitting and opaque regions, and represents one mask from the plurality of different masks formed by different portions of the pattern. One transmitting/opaque region, whilst being combined with its left-side neighboring region and whilst being combined with its right-side neighboring region, may form two different portions of the pattern, respectively. By rotating the disk about its axis, a different portion of the pattern (mask) is located in the optical path of the collected light impinging on the disk. Mask 28g in FIG. 5 depicts such an arrangement.

It should also be noted that such a mechanical filter may be replaced by a micro electromechanical structure (MEMS)

or a programmable liquid crystal display (LCD) whose construction and operation are known per se. The LCD segments are light valves which, when in the open mode, transmit or reflect light (depending on the kind of a liquid crystal material used therein), and, when in the closed mode, block light. A spatial filter in the form of a transmitting LCD is disclosed for example in U.S. Pat. No. 5,276,498.

Figure 7:
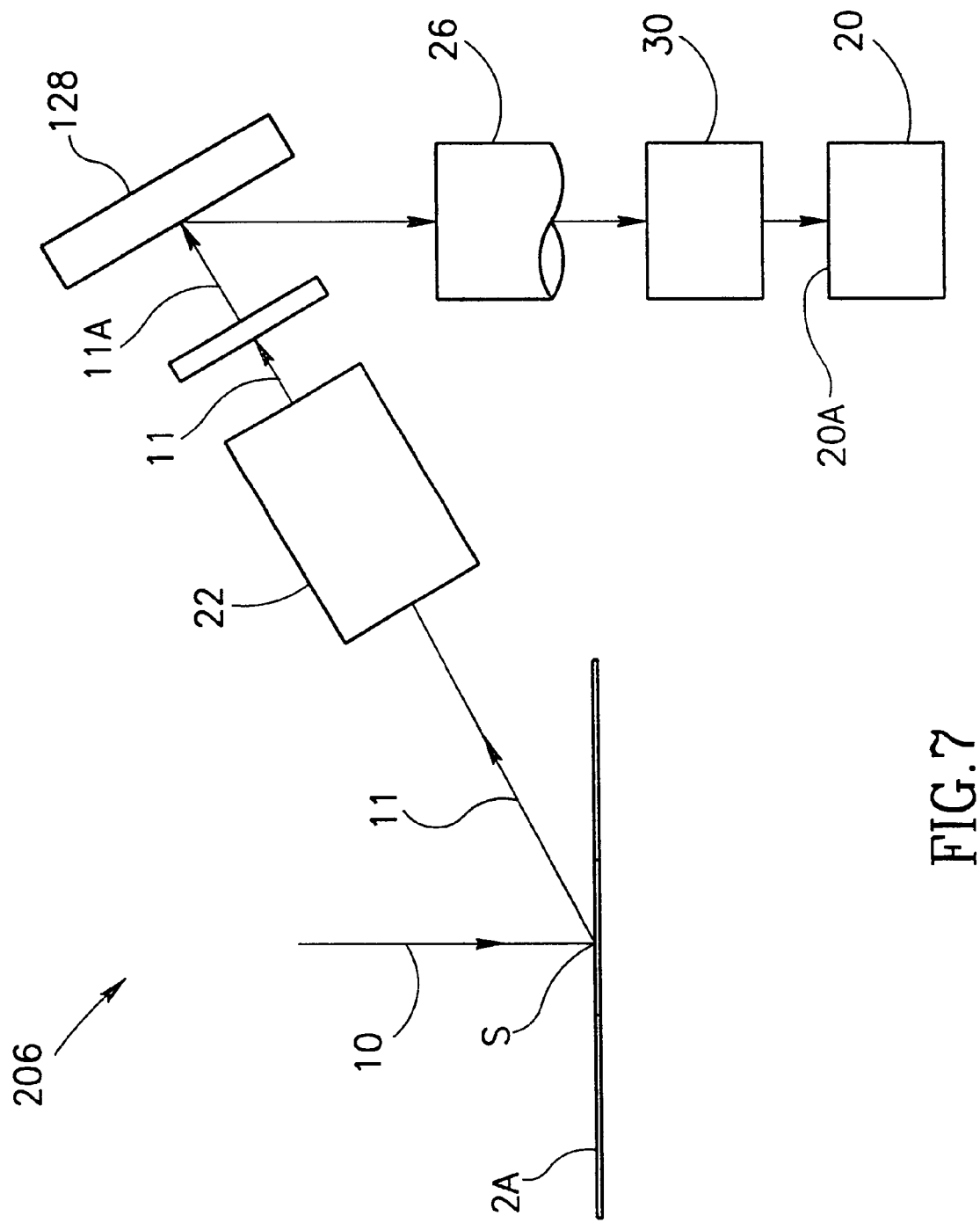

FIG. 7 illustrates by way of a block diagram another example of a detection unit, generally at 206. Here, a mask assembly 123 is either a reflective LCD or MEMS, the fiber bundle 26 being therefore positioned so as to receive collected light reflected from the filter 128. In the example of FIG. 7, similar to that of FIG. 6, the fiber bundle 26 may be of a non-imaging type.

Figure 8:
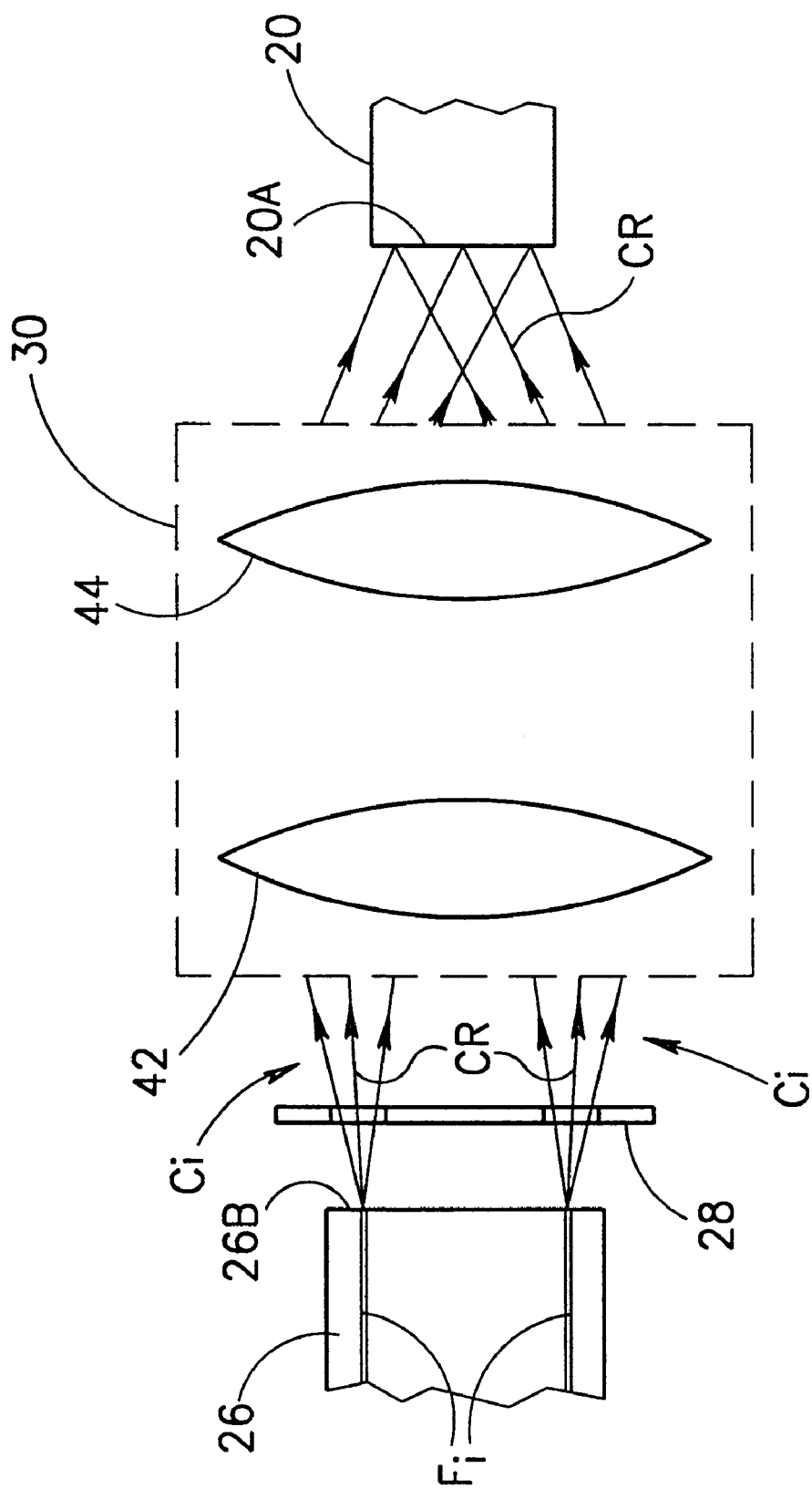
FIG. 8 is a beam diagram illustrating the main principles of operation of imaging optics of the detection unit of FIG. 3.

Reference is now made to FIG. 8 illustrating the main operational principles of the optical system 30. The optical system 30 projects the light collected by the mask assembly 28 onto the entire sensing surface 20a of the detector 20. The optical system 30 comprises a suitable number of lenses, two lenses 42 and 44 in the present example, and presents a telecentric imaging system, wherein the surface 20a is positioned at the location of the system's entrance pupil. The principles of telecentric imaging optics are known per se and therefore need not be more specifically described, except to note that such optics avoids distance-introduced magnification changes and maintains the same magnification of the image over a wide range of distances along the optical axis of the system. As known, light rays ensuing from each fiber $F_i$ propagate within a certain cone $C_i$ (solid angle). Chief rays CR of these light cones $C_i$ pass through the center of the entrance pupil 20a. The light cone $C_i$ ensuing from a point on the surface 26b of the fiber bundle 26, reaches the detector unit 20 and illuminates the region 20a. Thus, the optical system 30 projects each such light cone $C_i$ (i.e. images each point on the surface 26b) onto the same region of the sensing surface.

The provision of the optics 30 that projects the light collected by the mask assembly 28 onto the entire sensing surface 20a is associated with the following. The sensing surface of any detector typically has non-uniform sensitivity distribution. If the spatially separated light cones $C_i$ were projected onto correspondingly separated regions on the sensing surface, detected differences in the output signals produced by the detector might have been associated with the sensitivity differences of these regions and not with the differences in the scattered light. To avoid such an undesirable dependence between the output signal and the selected collection angle, optics 30 provides the illumination of the entire sensing surface by each one of the collected light components (selected angles).

As further seen in FIG. 8, the operational mask is designed such that two spatially separated light components $C_i$ (angles) ensuing from two fibers $F_i$, respectively, are picked out and transmitted onto the entire sensing surface 20a of the detector. Hence, due to the provision of the mask, one can choose a specific fiber to be imaged onto the detector, thereby choosing the collection angle.

Figure 9:
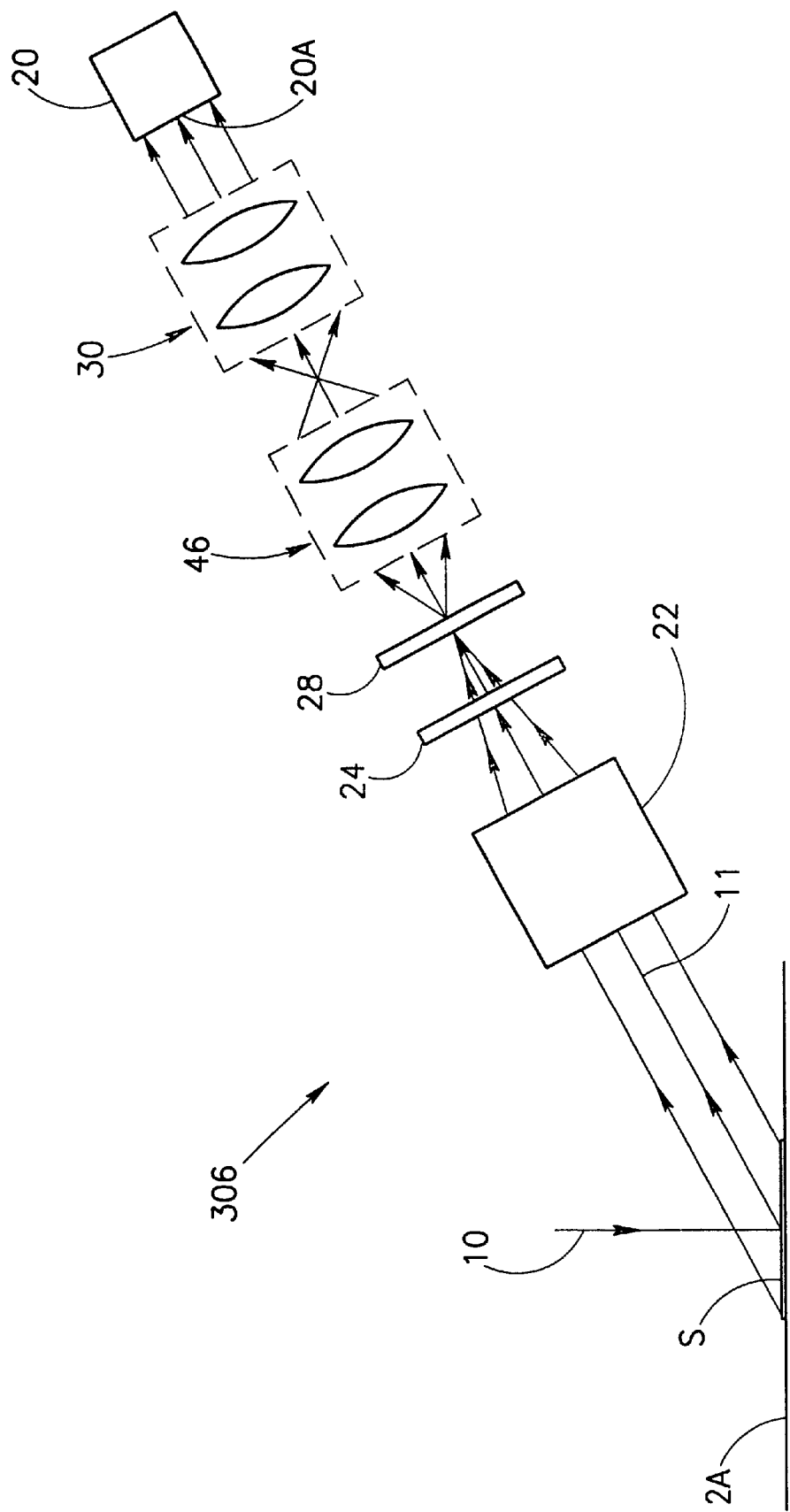
FIG. 9 is a schematic block diagram of the main components of a detection unit according to yet another example of the present invention, suitable for the apparatus of either of FIGS. 1 or 2.

FIG. 9 illustrates yet another example of a detection unit, generally at 306, in which the fiber bundle 26 is replaced by relay optics 46 (constituting image transmission means). The relay optics 46 is typically a multilens system that serves for maintaining a certain numerical aperture of the light propagation. The multilens system 46, similar to that of the fiber bundle 26, presents a physical opening that limits the amount of light that can pass through the system and transmits the image of the scan line S onto a desired location. As illustrated in the drawing in a self-explanatory manner, the telecentric optical system 30 operates as described above for projecting marginal rays ensuing from the multilens system 46 onto the entrance pupil defined by the surface 20a.

It should be specifically noted that the mask assembly 28 may be installed either in front of or after the relay optics 46. If the relay optics 46 is positioned in front of the mask assembly 28, the first glass surface of the relay optics is located in an entrance pupil of the light collecting optics 22.

As to the polarizer 24, it is understood that when using a coherent fiber bundle 26 as an image transmission means, the polarizer 24 should be accommodated in front of the fiber bundle, because optical fibers may depolarize the polarized light. However, when using the relay optics 46 as an image transmission means, both locations of the polarizer 24 relative to the relay optics 46 (i.e. in front of and after the relay optics) are suitable.

All the detection units operate in the above-described manner for collecting with their light collecting optics light scattered from the same scan line S at the same maximum elevation angle and at different maximum azimuth angles and forming the desired image of the scan line S. The detectors 20 generate data (electrical signals) representative of the detected light components. These data are received by the processor 7 and analyzed in a conventional manner so as to detect differences indicative of real defects existing within the scan line S.

In view of the above, the advantages of the present invention are self-evident. The provision of so designed light collecting optics 22 results in the increased signal-to-noise ratio in the collected light, which varies with the addressed wafer's layer. This is due to the fact that only those light components which are scattered from the scan line S with a preset maximum collection angle and which form an angular image of the scan line, are collected and directed towards the detector. The provision of the coherent fiber 26 or relay optics 46 provides for effective (i.e. free of distance-introduced changes) transmission of the image, thereby facilitating the mounting of the detection unit 20 at a desired location relative to the inspected wafer 2. The provision of the filter (e.g., the mask assembly 28) allows for significantly improving the inspection of articles. By selecting an appropriate mask, the azimuth and/or elevation of the collected light could be varied from their maximum values. The use of several detection units 6 observing the same region on the wafer 2, allows for meaningful comparison of data representative of light components, which are scattered by the same features on the wafer but propagate in different directions. It is also understood that by providing more than one dark-field imaging detection unit, oriented and operated as described above, the existing defects could not only be detected, but also successfully classified.

Those skilled in the art will readily appreciate that various modifications and changes may be applied to the preferred embodiments of the invention as hereinbefore exemplified without departing from its scope as defined in and by the appended claims.

What is claimed is:

1. An apparatus for optical inspection of an article, comprising an illumination unit generating incident radiation and illuminating a predetermined region on the article, and at least one detection unit, wherein said at least one detection unit comprises:

a light collecting optics that collects light scattered from an illuminated region with a predetermined constant maximum collection angle;

a filter selectively operable in an optical path of the collected light for selectively separating therefrom at least one light component propagating with a predetermined solid angle segment of the maximum collection angle and operable to enable detection of said at least one light component while preventing detection of light components propagating within a specific angular range of the maximum collection angle;

non-image transmission means located downstream from said filter for receiving the at least one light component propagating with a predetermined solid angle segment and transmitting the non-image to a desired location of the detector; and a detector having a sensing surface for receiving an output of said non-image transmission means and generating data representative thereof.

2. The apparatus according to claim 1, wherein said non-image transmission means comprises a fiber bundle.

3. The apparatus according to claim 1, wherein said non-image transmission means comprises relay optics.

4. The apparatus according to claim 1, wherein the detector operates in a perspective dark-field mode.

5. The apparatus according to claim 1, wherein said incident radiation impinges onto the article with substantially zero angle of incidence.

6. The apparatus according to claim 1, wherein said incident radiation impinges onto the article at an acute angle.

7. The apparatus according to claim 1, wherein said light collecting optics comprises a first optics forming a real image of the illuminated region to a second optics forming from said real image an angular image of the illuminate region.

8. The apparatus according to claim 1, wherein said light collecting optics further comprises a slit that has a shape and dimensions substantially identical to said real image of the illuminated region, and is mounted at a location substantially coinciding with a location of said real image formed by said first optics.

9. The apparatus according to claim 1, wherein the filter comprises a mask assembly defining at least one transmitting region with respect to the collected light.

10. The apparatus according to claim 9, wherein said mask assembly has a plurality of different masks providing for solid angle variations simultaneously along two mutually perpendicular axes, a selective one of the masks being installed in the optical path of the collected light when in the operative position of the filter.

11. The apparatus according to claim 10, wherein each mask defines at least one transmitting region with respect to the collected light, said at least one transmitting region corresponding to said predetermined solid angle segment of the maximum collection angle.

12. The apparatus according to claim 1, wherein said filter comprises a programmable LCD.

13. An apparatus for optical inspection of an article, comprising an illumination unit generating incident scanning radiation and illuminating a predetermined region on the article, and at least one detection unit, wherein said at least one detection comprises:

a light collecting optics that collects light scattered from the illuminated region and propagating within a predetermined constant maximum collection angle;

a filter selectively operable in the optical path of collected light for selectively separating therefrom at least one light component propagating with a predetermined solid angle segment of the maximum collection angle and operable to enable detection of said at least one light component while preventing detection of light components propagating within a specific angular range of the maximum collection angle;

non-image transmission means located downstream of said filter; and a detector having a sensing surface for receiving an output of said non-image transmission means.

14. The apparatus according to claim 13, wherein said non-image transmission means comprises a fiber bundle.

15. The apparatus according to claim 13, wherein said non-image transmission means comprises relay optics.

16. The apparatus according to claim 13, wherein the detector operates in a perspective dark-field mode.

17. The apparatus according to claim 13, wherein said incident radiation impinges onto the article with substantially zero angle of incidence.

18. The apparatus according to claim 13, wherein said incident radiation impinges onto the article at an acute angle.

19. The apparatus according to claim 13, wherein said light collecting optics comprises a first optics forming a real image of the illuminated region to a second optics forming from said real image an angular image of the illuminate region.

20. The apparatus according to claim 13, wherein said light collecting optics further comprises a slit that has a shape and dimensions substantially identical to said real image of the illuminated region, and is mounted at a location substantially coinciding with a location of said real image formed by said first optics.

21. The apparatus according to claim 13, wherein the filter comprises a mask assembly defining at least one transmitting region with respect to the collected light.

22. The apparatus according to claim 21, wherein said mask assembly has a plurality of different masks providing for solid angle variations simultaneously along two mutually perpendicular axes, a selective one of the masks being installed in the optical path of the collected light when in the operative position of the filter.

23. The apparatus according to claim 22, wherein each mask defines at least one transmitting region with respect to the collected light, said at least one transmitting region corresponding to said predetermined solid angle segment of the maximum collection angle.

24. The apparatus according to claim 13, wherein said filter comprises a programmable LCD.

* * * * *